(12) United States Patent
Carroll

(10) Patent No.: US 8,045,678 B2
(45) Date of Patent: Oct. 25, 2011

(54) DYNAMICALLY-VARIED BEAM ENERGY USING A TUNABLE MONOCHROMATIC X-RAY BEAM

(75) Inventor: Frank E. Carroll, Nashville, TN (US)

(73) Assignee: Mxisystems, Inc., Fairview, TN (US)

( * ) Notice: Subject to any disclaimer, the term of this patent is extended or adjusted under 35 U.S.C. 154(b) by 290 days.

(21) Appl. No.: 12/244,219

(22) Filed: Oct. 2, 2008

(65) Prior Publication Data

US 2009/0238339 A1    Sep. 24, 2009

Related U.S. Application Data

(60) Provisional application No. 61/038,438, filed on Mar. 21, 2008.

(51) Int. Cl.
*A61N 5/10* (2006.01)
(52) U.S. Cl. ............................................. 378/65; 378/95
(58) Field of Classification Search ...................... 378/65
See application file for complete search history.

(56) References Cited

U.S. PATENT DOCUMENTS

| | | | |
|---|---|---|---|
| 6,687,333 B2 * | 2/2004 | Carroll et al. ................. | 378/119 |
| 2005/0020869 A1 | 1/2005 | Hainfeld et al. | |
| 2005/0080019 A1 * | 4/2005 | Wang .............................. | 514/23 |
| 2005/0259787 A1 * | 11/2005 | Carroll ........................... | 378/65 |
| 2006/0008047 A1 | 1/2006 | Zhou et al. | |
| 2006/0173352 A1 | 8/2006 | Lilge et al. | |
| 2007/0189444 A1 | 8/2007 | Van Steven-Daal et al. | |
| 2011/0038455 A1 * | 2/2011 | Silver et al. ...................... | 378/62 |

FOREIGN PATENT DOCUMENTS

WO    WO 2005/110495 A1    11/2005

OTHER PUBLICATIONS

International Search Report and Written Opinion of the International Searching Authority issued in PCT/US2009/037594, dated May 29, 2009, 10 pgs.

* cited by examiner

*Primary Examiner* — Hoon Song
*Assistant Examiner* — Mona M Sanei
(74) *Attorney, Agent, or Firm* — Cooley LLP

(57) ABSTRACT

In one embodiment, a method includes applying an output of a substantially monochromatic x-ray source to a target tissue along a first path, tuning the output of the substantially monochromatic x-ray beam source, and applying an output of a substantially monochromatic x-ray beam source to a target tissue along a second path different from the first path. The energy of the output of the substantially monochromatic x-ray beam source at the target tissue substantially corresponds to a binding energy level of an electron shell in an atom within the target tissue along the first path. The tuning tunes the substantially monochromatic x-ray beam source such that an energy of the output of the substantially monochromatic x-ray beam source at the target tissue along the second path substantially corresponds to a binding energy level of an electron shell in an atom within the target tissue.

19 Claims, 9 Drawing Sheets

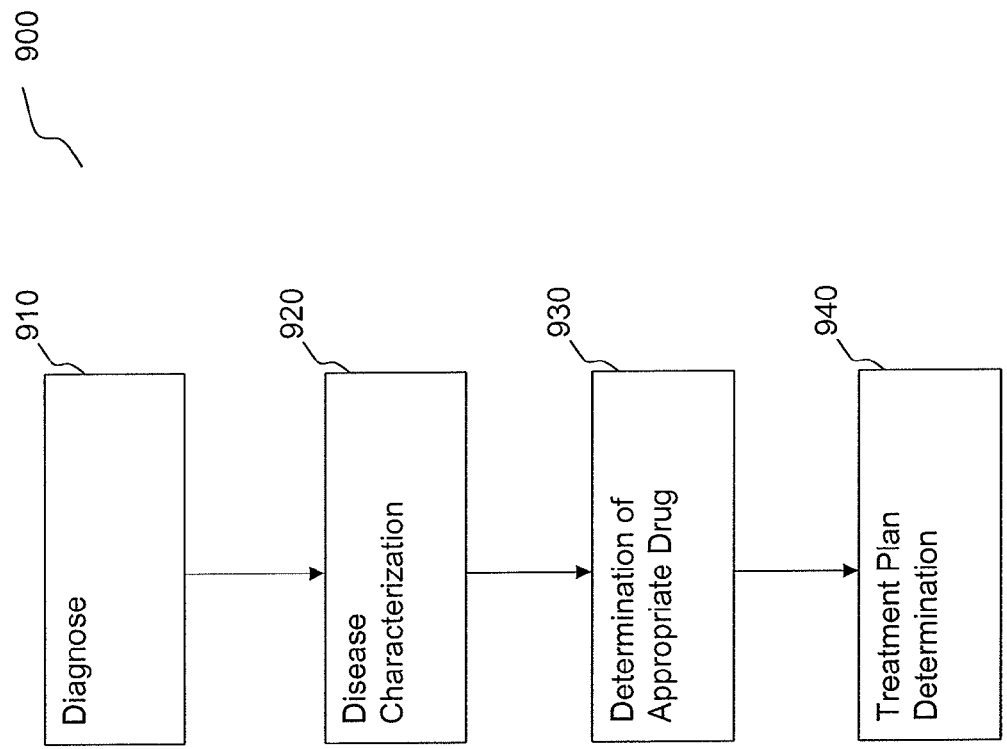

DYNAMICALLY-VARIED BEAM ENERGY USING A TUNABLE MONOCHROMATIC X-RAY BEAM

CROSS-REFERENCE TO RELATED APPLICATION

This application claims priority to U.S. Patent Application Ser. No. 61/038,438, filed on Mar. 21, 2008 and entitled "Dynamically-Varied Beam Energy using A Tunable Monochromatic X-ray Beam," which is incorporated herein by reference in its entirety.

BACKGROUND

The invention relates generally to dynamically-varied beam energy using a tunable monochromatic x-ray beam. For example, in radiation therapy the energy of such an x-ray beam can be varied during treatment to compensate for changes in the position of a tumor relative to a beam source and the body of a patient such that an optimally minimal effective dose of radiation is administered.

Various radiation therapies, or radiotherapies, including, for example, intensity modulated radiotherapy (IMRT), image guided radiotherapy (IGRT), proton therapy, electron beam therapy, and gamma knife treatments are known. Such radiotherapies typically require that lethal doses of radiation be applied to a tumor for the treatment to be effective, and such radiotherapies typically are planned and delivered in a fashion using one specific beam energy for any given therapy session. These doses of radiation are problematic, however, because they are as lethal to normal tissues as they are to tumors. The doses of radiation administered in such radiotherapies are predominantly distributed throughout a tumor's tissues in a pattern that is somewhat random on a microscopic or intracellular level. This results in singlet oxygen and other ionized compounds that are damaging to intracellular organelles of both the tumor tissues and surrounding healthy tissues.

Furthermore, because these radiolytic events are random, they may or may not lead to severe damage to the DNA that resides in the nucleus of a tumor's cells. Additionally, much of the damage induced by known radiotherapies can be repaired by the cell or, alternatively, the cell itself may not be sensitive to the radiation in certain phases of its reproductive life. These characteristics of radiolytic events and cell development typically require that large doses of radiation are given repeatedly in multiple sessions over several days or weeks to effectively destroy the tumor cells.

Auger Cascade Radiotherapy (ACR) is an alternative radiotherapy that uses non-lethal doses of radiation and is less random than other current radiotherapies. ACR entails incorporation of target atoms having high atomic number onto or into the double helical structure of the DNA of tumor cells. A monochromatic photon beam, for example an x-ray beam, with an energy at or slightly above the binding energy of the inner electron shells of the target atoms and directed at the tumor can displace or eject electrons from the inner suborbital shells of the target atoms. The displaced electrons become photoelectrons that distribute their energy within nanometers of the DNA onto which the target atoms are incorporated, resulting in damage to organelles and breaks in the double helix structure of DNA in surrounding cells. The displaced electrons leave voids in the orbits from which they are ejected. These voids are filled by electrons that tend to cascade from higher energy orbits into the voids. As electrons from higher energy orbits cascade into the voids left by the displaced electrons, energy corresponding to the difference in the energy level of the higher level orbit and the energy level of the orbit from which the electron was displaced is emitted in the form of photons. These photons also distribute their energy within nanometers of the DNA onto which the target atoms are incorporated. The cascading electrons also leave voids in their original orbits, which are similarly filled by cascading electrons from even higher energy orbits. This cascading process is known as Auger cascade.

The repeated emission of photons from the target atoms during Auger cascade results in very intense localized radiation within a few nanometers of the target atoms. Because ACR is less random and more localized that other radiotherapies, and because it uses energy emitted from stimulated target atoms, far less external radiation is necessary for effective treatment. Typically, the dose of external radiation required is three to five time less than a dose lethal to surrounding tissues.

SUMMARY

In one embodiment, a method includes applying an output of a substantially monochromatic x-ray beam source to a target tissue along a first path, tuning the output of the substantially monochromatic x-ray beam source, and applying an output of a substantially monochromatic x-ray beam source to a target tissue along a second path different from the first path. The energy of the output of the substantially monochromatic x-ray beam source at the target tissue substantially corresponds to a binding energy level of an electron shell in an atom within the target tissue along the first path. The tuning tunes the substantially monochromatic x-ray beam source such that an energy of the output of the substantially monochromatic x-ray beam source at the target tissue along the second path substantially corresponds to a binding energy level of an electron shell in an atom within the target tissue.

In another embodiment, an apparatus comprises a tunable substantially monochromatic x-ray beam source, a positioning device, an image detector, and a processor. The positioning device is configured to change position of the output of the tunable substantially monochromatic x-ray beam source relative to a patient. The image detector is configured to image a target tissue within a body of a patient to produce data associated with images of the target tissue within the body of the patient. The processor is communicatively coupled to the image detector and the tunable substantially monochromatic x-ray beam source, and is configured to receive the data associated with images of the target tissue from the image detector. Additionally, the processor is configured to effect an adjustment to the tunable substantially monochromatic x-ray beam source such that an energy of the output of the substantially monochromatic x-ray beam source at the target tissue substantially corresponds to a binding energy level of an electron shell in an atom within the target tissue based on the data associated with images of the target tissue.

BRIEF DESCRIPTION OF THE DRAWINGS

FIG. 9 shows a flowchart of a process for pre-treatment radiotherapy planning, according to an embodiment.

DETAILED DESCRIPTION

Current radiotherapy techniques including ACR, suffer from several disadvantages. For example, radiation therapy planning and treatment for any given treatment session is limited to a single beam energy or wavelength. Because tumors are treated in vivo and healthy tissues scatter or impede radiation directed to a tumor or other target tissue, use of single-beam energy precludes treatment based on application of a minimal dose of external radiation along each of a number of paths through the body of a patient to the target tissue. Thus, a need exists for improved radiotherapy using dynamically-varied radiation energy.

Here, in one or more embodiments, when optimal energies for radiotherapy are selected during pre-treatment planning, the radiation beam can be sent along a given path from a radiation source to a target tissue at any angle or from any direction such that the peak energy is modified dynamically as the patient receives radiation therapy from a radiation beam source to minimize radiation exposure and maximize treatment efficacy. In broad terms, one or more embodiments described herein can deliver radiation at a specific energy to a target tissue along multiple paths. In some embodiments, an x-ray beam source can be repositioned and dynamically tuned during a radiotherapy treatment to radiate a tumor in the body of a patient with x-ray beams having a specific predetermined energy at the tumor from multiple directions or at multiple angles.

Figure 1:
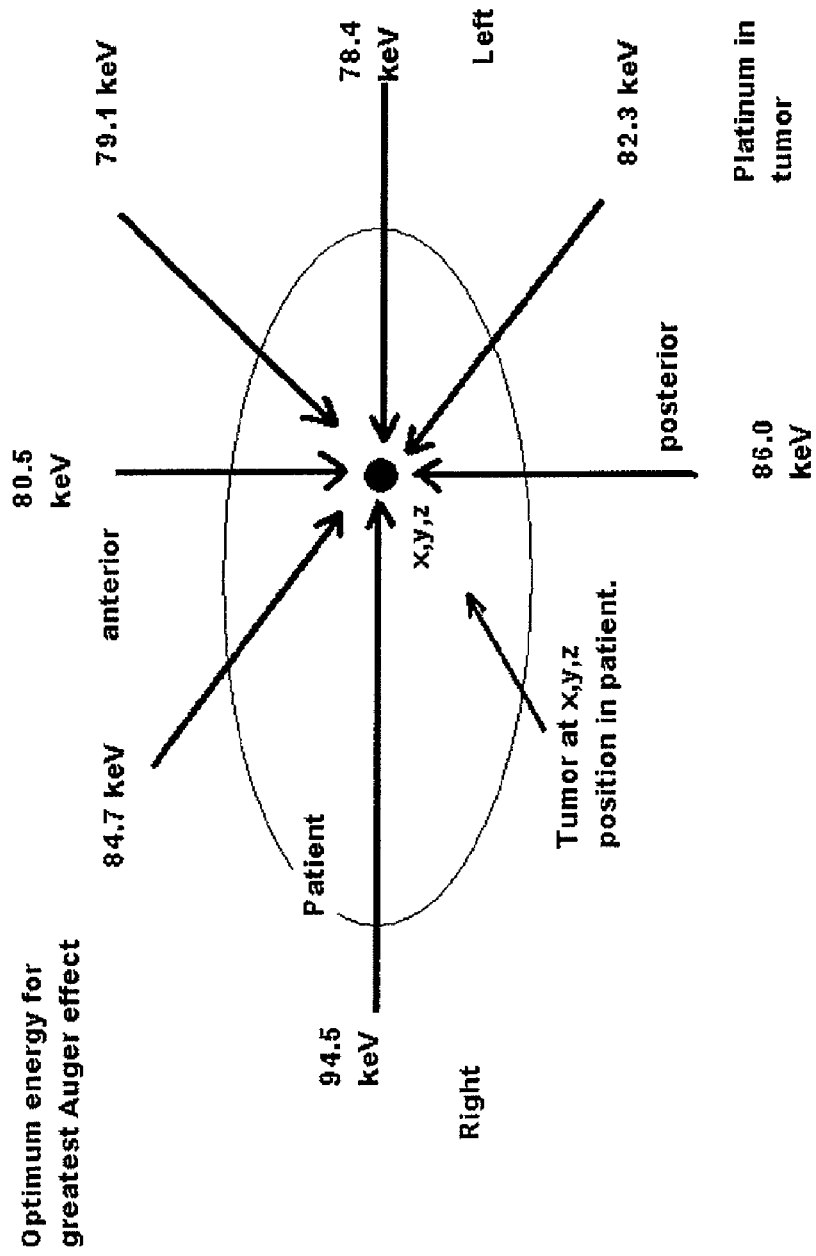
FIG. 1 illustrates a diagram representing the peak energy along each of multiple paths for treating a tumor within the body of a patient, according to an embodiment.

FIG. 1 illustrates a diagram representing the peak energy along each of multiple paths for treating a tumor within the body of a patient, according to an embodiment. FIG. 1 shows the effect of a radiation beam passing through the body of the patient to the tumor from multiple directions or angles. Specifically, FIG. 1 illustrates a radiation beam radiating a tumor in the body of the patient (shown from a top view) along seven different paths. The radiation beam has a unique energy along each path. The radiation beam along a first path has a peak energy of 86.0 keV and is incident on the tumor from a position posterior to the patient. The radiation beam along a second path has a peak energy of 82.3 keV and is incident on the tumor from a position left and posterior to the patient. The radiation beam along a third path has a peak energy of 78.4 keV and is incident on the tumor from a position left of the patient. The radiation beam along a fourth path has a peak energy of 79.1 keV and is incident on the tumor from a position left and anterior to the patient. The radiation beam along a fifth path has a peak energy of 80.5 keV and is incident on the tumor from a position anterior to the patient. The radiation beam along a sixth path has a peak energy of 84.7 keV and is incident on the tumor from a position right and anterior to the patient. The radiation beam along a seventh path has a peak energy of 94.5 keV and is incident on the tumor from a position right of the patient. The body of the patient is shown from a top view and represented as an oval. The tumor, at some arbitrary position x, y, z within the body of the patient, is typically not centered in the body of the patient. Thus, the radiation beam traverses through a different amount or distance of the body of the patient when emitted from each direction or angle. Because the radiation beam is scattered and/or attenuated to some extent while traversing the body of the patient toward the tumor, the energy of the radiation beam at the tumor is altered by a different amount along each path for each direction or angle. Accordingly, the pre-selected peak energy (e.g., optimum or desired) of the radiation beam is adjusted for each path, direction, or angle such that peak energy of the radiation beam at the tumor is substantially the same for each path, direction, or angle and provides the greatest Auger cascade effect at the tumor. Generally, a greater distance between the surface of the body and the tumor involves greater peak energy of the radiation beam.

Although FIG. 1 shows the paths of the radiation beam being defined within a common horizontal plane, it should be understood that each path of the radiation beam need not be within the same horizontal plane (or transverse plane). For example, the paths of the radiation beam can alternatively be directed to the tumor from different angles with respect to a transverse plane, as well as different angles with respect to a sagittal plane and/or coronal plane. In some embodiments, one or more paths of the radiation beam can be configured to minimize the amount of tissue in the body of the patient through which the radiation beam propagates to radiate a tumor. In other embodiments, one or more paths of the radiation beam can be directed to prevent the radiation beam from radiating an organ, an implant, and/or some other object in the body of the patient. For example, the paths of the radiation beam can be directed to the tumor at an angle with respect to one or more planes such that the radiation beam radiates the tumor without significantly radiating organs, implants, and/or other objects in the body of the patient other than the tumor. Additionally, in some embodiments, more than one radiation source can be included to provide radiation to the tumor along two or more paths at a given time.

As an example, an x-ray beam source can be positioned relative to a tumor within the body of a patient to radiate the tumor from a particular direction and tuned such that the x-ray beam produced by the x-ray beam source has a particular energy at the tumor after propagating along the path from the x-ray beam source to the tumor. The x-ray beam source can then be repositioned such that an x-ray beam produced by the x-ray beam source propagates along a different path from the x-ray beam source to the tumor to radiate the tumor from a different direction. The x-ray beam source can be dynamically retuned such that an x-ray beam produced by the x-ray beam source in the current position has substantially the same effective energy at the tumor after propagating along the path from the x-ray beam source to the tumor as the x-ray beam from the previous position had at the tumor after propagating along the prior path. This process of repositioning and retuning can be repeated to radiate the tumor from numerous directions with x-rays having a specific energy for each direction. Thus, the tumor can be more effectively radiated from multiple directions and the amount of radiation exposure can be lowered by using only the energy appropriate for each x-ray beam direction.

In some embodiments, the repositioning and retuning can be used with Auger cascade techniques to implement ACR more effectively. For example, target atoms can be incorporated into or onto the DNA of a tumor. The tumor can be radiated with energy from an x-ray beam source tuned such that the x-ray beam produced by the x-ray beam source has an energy at the tumor sufficient to induce Auger cascade in the target atoms. In other words, the x-ray beam produced by the x-ray beam source has an energy at the tumor greater than or equal to the binding energy of an electron in an inner orbit of the target atom. The x-ray beam source can be repositioned and dynamically retuned to radiate the tumor from other directions to radiate the tumor sufficiently with minimal or less harm to healthy tissues surrounding the tumor.

Figure 2:
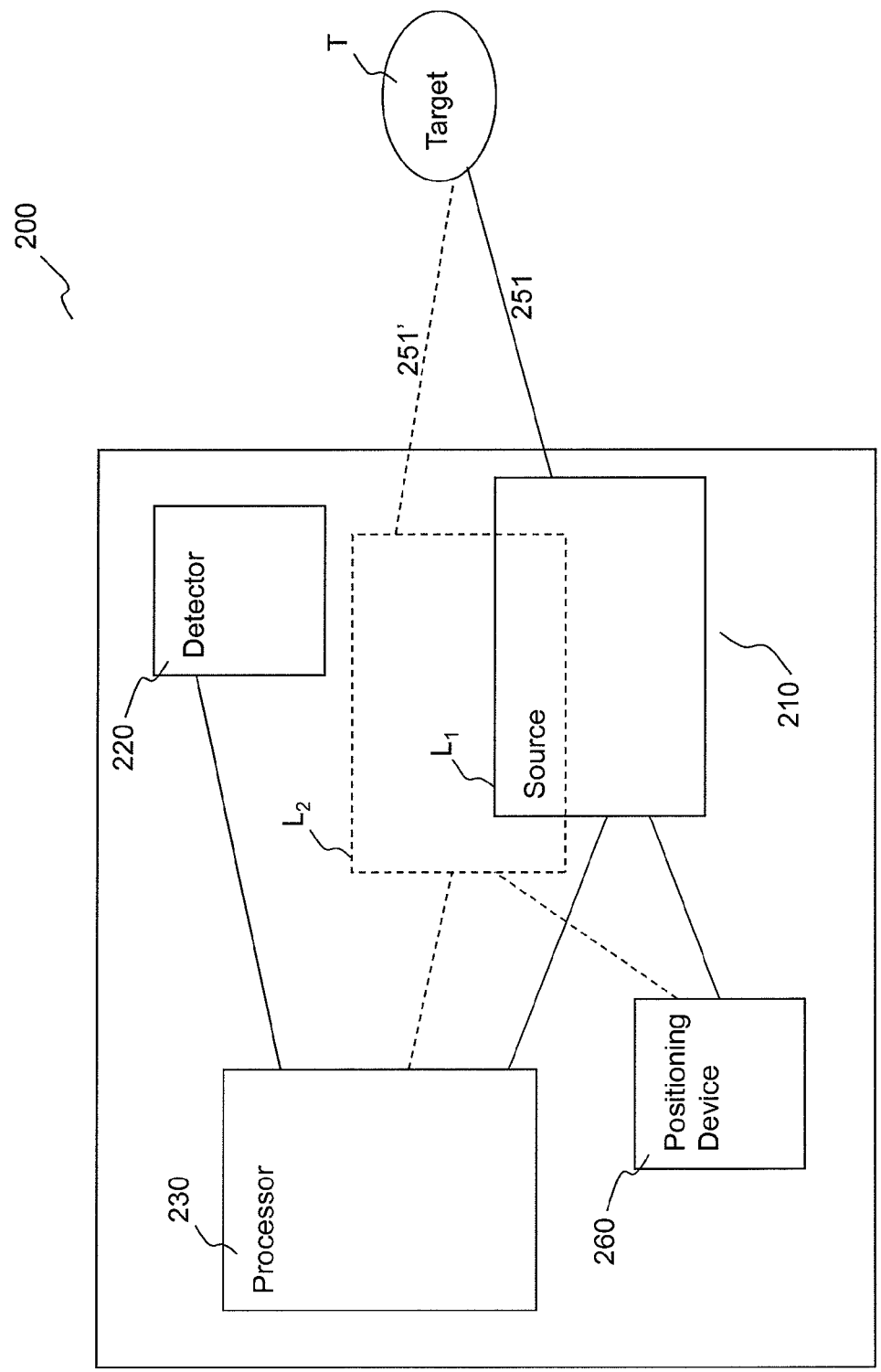
FIG. 2 shows a system block diagram of a radiotherapy system, according to an embodiment.

FIG. 2 shows a system block diagram of a radiotherapy system, according to an embodiment. As shown in FIG. 2, radiotherapy system 200 includes tunable radiation source 210 and processor 230. Tunable radiation source 210 at location $L_1$ outputs a radiation beam to radiate target T with radiation along path 251. Tunable radiation source 210 can be repositioned to location $L_2$ such that target T is radiated along path 251'. Tunable radiation source 210 can receive tuning signals from processor 230 such that radiation emitted from tunable radiation source 210 has an energy at target T that is substantially the same when target T is radiated along path 251 and path 251'. Target T can be, for example, a tissue or a tumor within the body of a patient.

In some embodiments as shown in FIG. 2, radiotherapy system 200 can include an optional detector 220 to detect transmitted or scattered radiation from target T. Detector 220 can be, for example, an imager based on a charge-coupled device (CCD) or a complementary metal-oxide-semiconductor (CMOS) device. Alternatively, detector 220 can be a reusable imaging media for use in direct radiography and/or computed radiography such as, for example, reusable image plates. Alternatively, detector 220 can be a single-use media. In other embodiments, detector 220 can be positioned opposite tunable radiation source 210 such that target T is between detector 220 and tunable radiation source 210. In such embodiments, detector 220 can detect radiation propagating through and/or radiation emitting from target T. Detector 220 can be in communication with processor 230 and send signals associated with radiation detected by detector 220 to processor 230. Such signals can include, for example, image data and/or intensity data. Processor 230 can receive and interpret signals sent by detector 220 and make adjustments such as, for example, tuning or positioning tunable radiation source 210 relative to target T.

Tunable radiation source 210 can be any radiation source capable of dynamic tuning. Tuning includes, for example, adjusting, modifying or selecting the wavelength (frequency and/or energy) of radiation emitted by tunable radiation source 210 during operation of radiation source. Tuning can also include adjusting, modifying or selecting the beam size, beam shape, and/or flux (fluence and/or intensity) of radiation emitted during operation of radiation source, for example. The tuning can be dynamic in the sense that the tuning can be performed during operation of the tunable radiation source including, for example, changes in the tuning within relatively short periods of time such as 0.05-0.10 sec.

Figure 3:
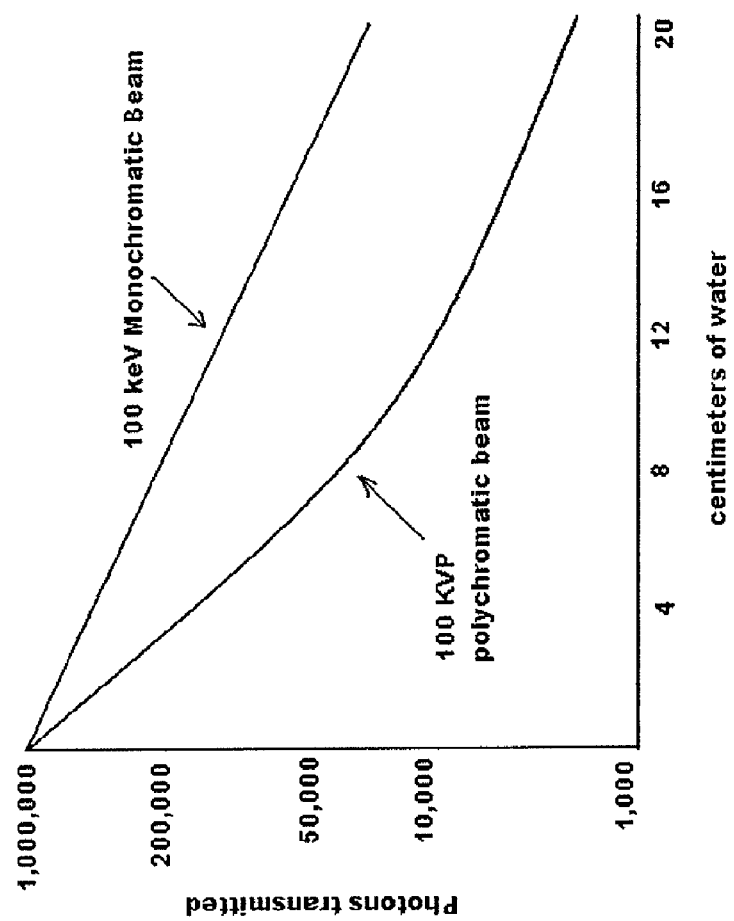
FIG. 3 shows a graph of the intensities of a monochromatic beam and a polychromatic beam through different thicknesses of water.

In some embodiments, for example, tunable radiation source 210 can be a substantially monochromatic radiation source. In yet other embodiments, tunable radiation source 210 can be a tunable polychromatic radiation source. FIG. 3 shows a graph of the intensities of a substantially monochromatic beam and a polychromatic beam through different thicknesses of water. Substantially monochromatic beams containing photons that are all at approximately the same energy scatter and are absorbed in a simple linear function dependent on depth. A polychromatic beam on the other hand contains photons of many different energies, some of which are quite "soft" or of low energy and are rapidly absorbed and scattered at a greater rate than photons of higher energy, which are also present in the beam. This latter effect is called beam hardening. It is one of the factors that can be taken into account as any broad-spectrum radiation beam traverses a patient. While beam hardening is less of a factor with monochromatic beams, it can be considered and compensated for in radiation planning for ACR or other radiotherapy techniques.

In yet other embodiments, tunable radiation source 210 can be a tunable pulsed radiation source such as, for example, a pulsed x-ray source. In some such embodiments, a tunable pulsed x-ray source produces a beam of x-ray radiation by emitting multiple pulses of x-ray radiation. Thus, in some embodiments, a radiation beam produced by tunable radiation source 210 can be a sequence of two or more radiation pulses.

Pulsed radiation sources can be particularly suitable as tunable radiation sources because such radiation sources can be tuned between emissions of radiation pulses. One such source is the system for generating tunable pulsed monochromatic x-rays described in U.S. Pat. No. 6,687,333 B2, which is incorporated herein by reference in its entirety. This system produces pulsed monochromatic x-rays and can be tuned by selecting the energy level of electrons emitted by an RF LINAC. Thus, this system is capable of producing a beam of pulsed x-ray radiation that can be varied in energy during operation.

Processor 230 can be operatively coupled to tunable radiation source 210 such that processor 230 and tunable radiation source 210 are in communication. Processor 230 can send signals to tunable radiation source 210 to tune the energy of tunable radiation source 210. In some embodiments, tunable radiation source 210 includes a positioning device (not shown) capable of repositioning tunable radiation source 210 in response to signals from processor 230 or some other input including, for example, input from a user or another processor. In other embodiments, tunable radiation source 210 can be coupled to a positioning device capable 260 (shown in FIG. 2) for repositioning the tunable radiation source with respect to target T. Alternatively, the positioning device can position the target relative to tunable radiation source 210. In some such embodiments, the positioning device can be in communication with processor 230 or some other device including, for example, another processor to control positioning of tunable radiation source 210. Such positioning devices can include, for example, stepper motors, solenoids, articulated mechanical arms, rail-mounted fixtures, and/or track-mounted fixtures.

Some embodiments include a processor and a related processor-readable medium having instructions or computer code thereon for performing various processor-implemented operations. Such processors can be implemented, for example, as hardware modules such as embedded microprocessors, microprocessors as part of a computer system, Application-Specific Integrated Circuits ("ASICs"), and Programmable Logic Devices ("PLDs"). Such processors can also be implemented as one or more software modules in programming languages as Java, C++, C, assembly, a hardware description language, or any other suitable programming language. A processor according to some embodiments includes media and computer code (also can be referred to as code) specially designed and constructed for the specific purpose or purposes. Examples of processor-readable media include, but are not limited to: magnetic storage media such as hard disks, floppy disks, and magnetic tape; optical storage media such as Compact Disc/Digital Video Discs ("CD/DVDs"), Compact Disc-Read Only Memories ("CD-ROMs"), and holographic devices; magneto-optical storage media such as floptical disks; solid-state memory such as solid-state drives ("SSDs") and FLASH memory; and read-only memory ("ROM") and random-access memory ("RAM") devices. Examples of computer code include, but are not limited to, micro-code or micro-instructions, machine instructions, such as produced by a compiler, and files containing higher-level instructions that are executed by a computer using an interpreter. For example, an embodiment of the invention may be implemented using Java, C++, or other object-oriented programming language and development tools. Additional examples of computer code include, but are not limited to, control signals, encrypted code, and compressed code.

In some embodiments, processor 230 can implement a treatment plan as described in further detail below. A treatment plan can indicate, for example, the types and/or amount of tissue or material that will be traversed by a radiation beam output from tunable radiation source 210 before the radiation beam reaches target T, the desired energy of the radiation beam at target T, the size of target T, and/or positions from which tunable radiation source 210 will radiate target T during a radiotherapy treatment session. Processor 230 can implement a treatment plan by, for example, determining an energy at which a radiation beam should be emitted from tunable radiation source 210 to radiate target T with a desired energy after the radiation beam propagates through the type and/or amount of tissue or material specified in the radiation plan, and sending signals to tunable radiation source 210 to cause tunable radiation source 210 to emit a radiation beam with appropriate radiation energy. Furthermore, in some embodiments, processor 230 can send signals to tunable radiation source 210 or a positioning device to which tunable radiation source 210 is coupled, to cause tunable radiation source 210 to radiate target T from multiple directions and/or along multiple paths according to a predetermined pattern of positions. In other embodiments, processor 230 can use information about the size and/or shape of target T to determine positions from which to radiate target T. Information about the size and/or shape of target T can be predetermined and provided to processor 230 as part of the treatment plan. Alternatively, processor 230 can determine appropriate positions for radiation emissions based on, for example, signals received from detector 220.

In some embodiments, processor 230 can tune and/or reposition tunable radiation source 210 to compensate for changes in position of target T. Processor 230 can use signals received from detector 220 to identify a position of target T with respect to tunable radiation source 210 at various times to track or detect movement and/or changes in position of target T. Processor 230 can then tune and/or reposition tunable radiation source 210 or a patient positioning chair/table to compensate for a change in the position of target T such that the radiation beam from tunable radiation source 210 has the desired energy at target T. Such embodiments can be especially useful when target T is a tissue within the body of a patient and the patient may shift position during treatment, including relatively large position changes and relatively small position changes such as breathing.

Figure 4:
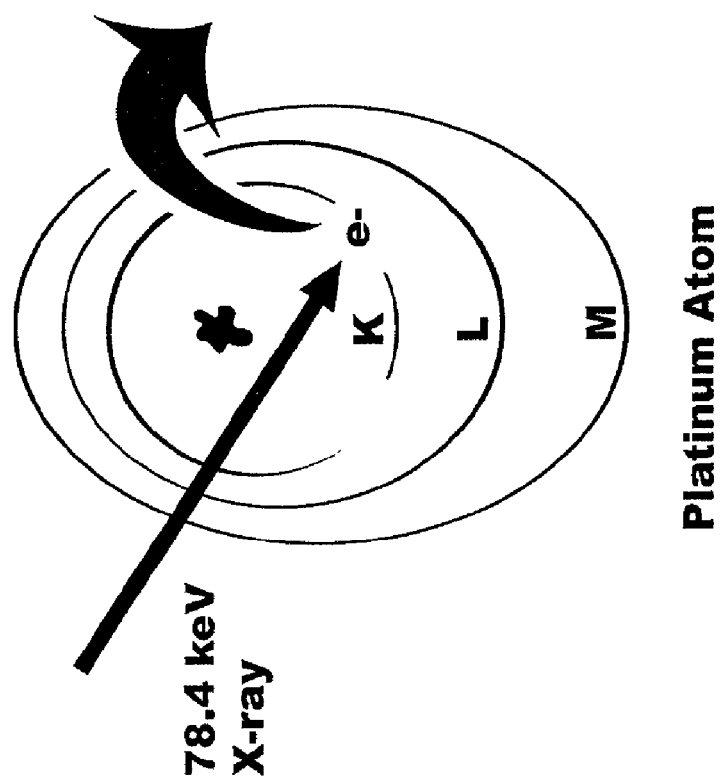
FIG. 4 shows a diagram representing a electron ejected from its orbit by a photon at or above the binding energy of the electron's orbit.
Figure 5:
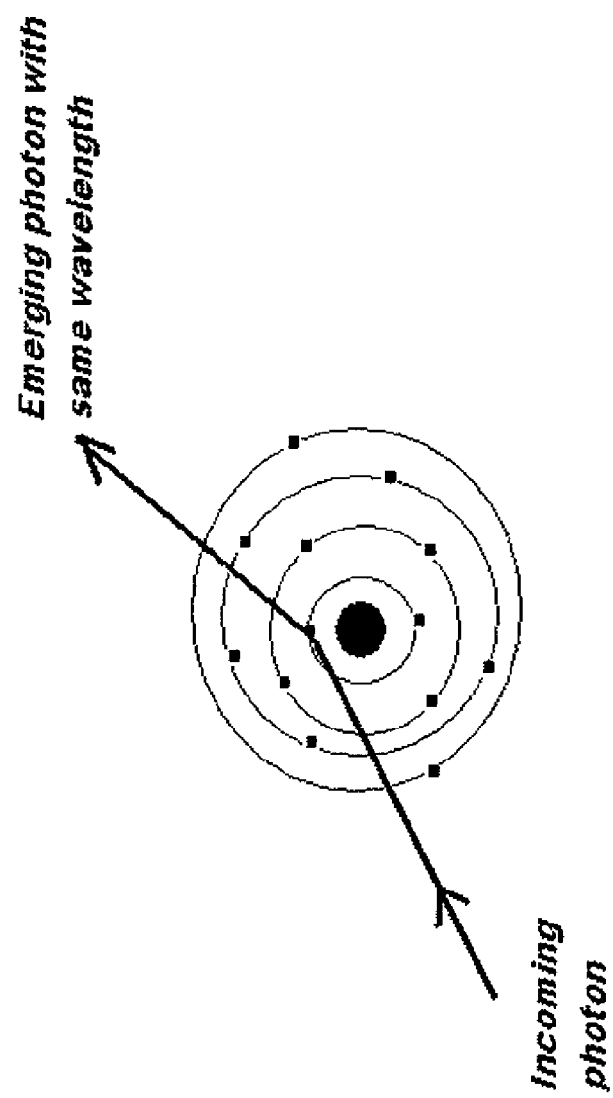
FIG. 5 illustrates a diagram representing unmodified or coherent scattering.
Figure 6:
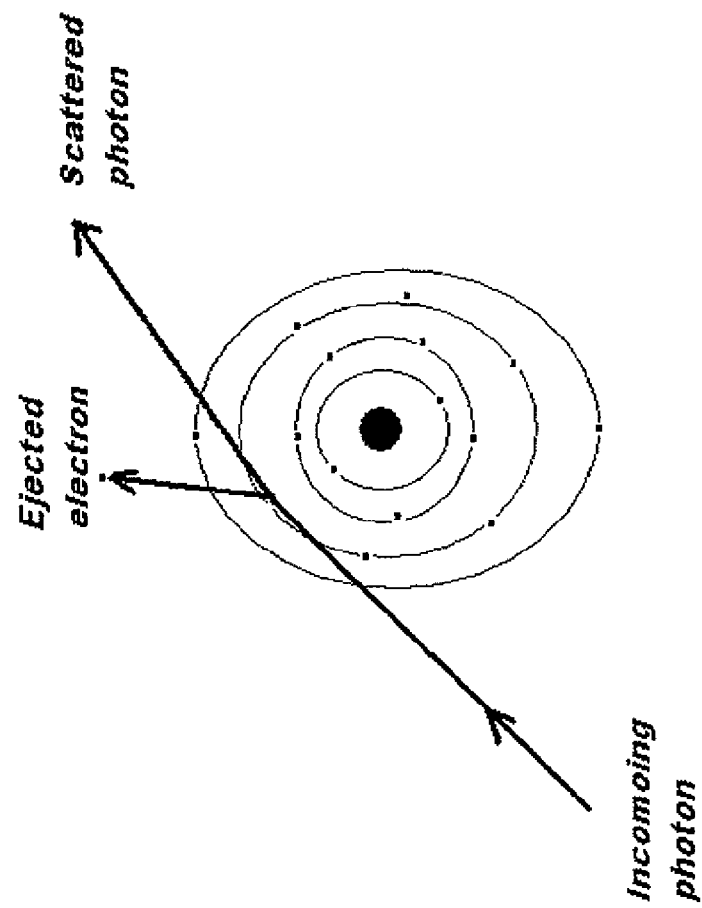
FIG. 6 illustrates a diagram representing a Compton collision resulting in an ejected electron and a scattered photon.

In some embodiments, radiotherapy system 200 can be used in ACR. FIGS. 4-7 illustrate the process of Auger cascade. As shown in FIG. 4, an electron is ejected from its orbit by a photon at the binding energy of the electron's orbit to initiate an Auger cascade. In FIG. 4, the x-ray photon is completely absorbed because it matches the binding energy of the ejected electron. FIG. 5 illustrates a diagram representing unmodified or coherent scattering in which a photon does not have sufficient energy to displace an electron and is absorbed and immediately remitted at an angle with unchanged energy. Such scattering does not result in Auger cascade. FIG. 6 illustrates a diagram representing a Compton collision resulting in an ejected electron and a scattered photon. Such a collision is capable of initiating Auger cascade similar to the collision in FIG. 4. In FIG. 6, however, the incoming photon has a higher energy than the binding energy of the ejected electron resulting in a scattered photon. The scattered photon has a lower energy than the incoming photon. If the scattered photon has a higher energy than the binding energy of an electron in another atom, the scattered photon can cause that electron to be ejected from its orbit, resulting in another Auger cascade. These different absorption and scattering processes are involved in modifying the ultimate effective energy of a radiation beam, for example, an x-ray beam, as it approaches a target tissue within the body of a patient.

Figure 7:
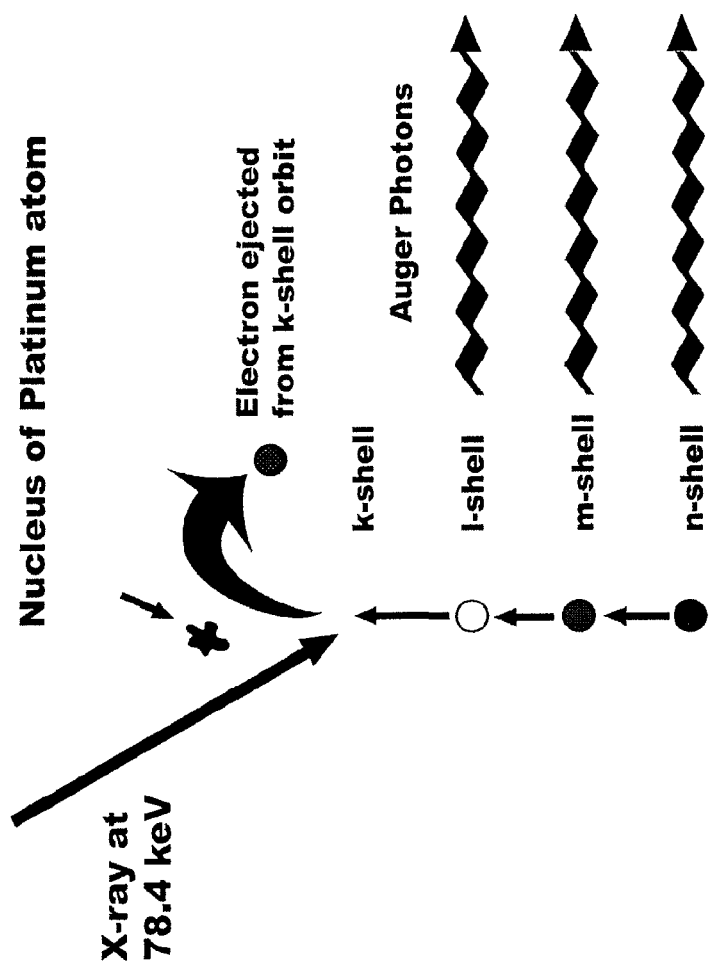
FIG. 7 illustrates a diagram representing photons released during Auger cascade.

FIG. 7 illustrates a diagram representing photons released during Auger cascade. An incoming x-ray photon has energy equal to that of the binding energy of the k-shell of a platinum atom. When the incoming x-ray photon is absorbed by the platinum atom, an electron is ejected from the k-shell of the platinum atom. A series of Auger photons are emitted from the platinum atom as an electron from the l-shell releases energy to fill the void in the k-shell, an electron from the m-shell releases energy to fill the void in the l-shell, and an electron from the n-shell releases energy to fill the void in the m-shell. The photons emitted from the platinum atom during Auger cascade can destroy nearby cell organelles and/or cause breaks in the double helical structure of the DNA in nearby cells, thus reducing the amount of external radiation necessary to effectively treat a target tissue such as, for example, a tumor.

Embodiments implementing ACR include an additional step of incorporating a target atom into or onto the double helix structure DNA of target T. Target atoms can be, for example, atoms with a high atomic number (high-Z atoms) such as platinum. Such target atoms define a stable target toward which x-ray radiation can be directed to knock or eject electrons from the inner orbits of the target atoms. Alternatively, target atoms may be radioactive target atoms that decay in such a way as to create Auger cascades when the target atom is destroyed by, for example, application of external radiation. As described above, Auger cascade in target atoms can reduce the amount of external radiation required for effective treatment.

Figure 8:
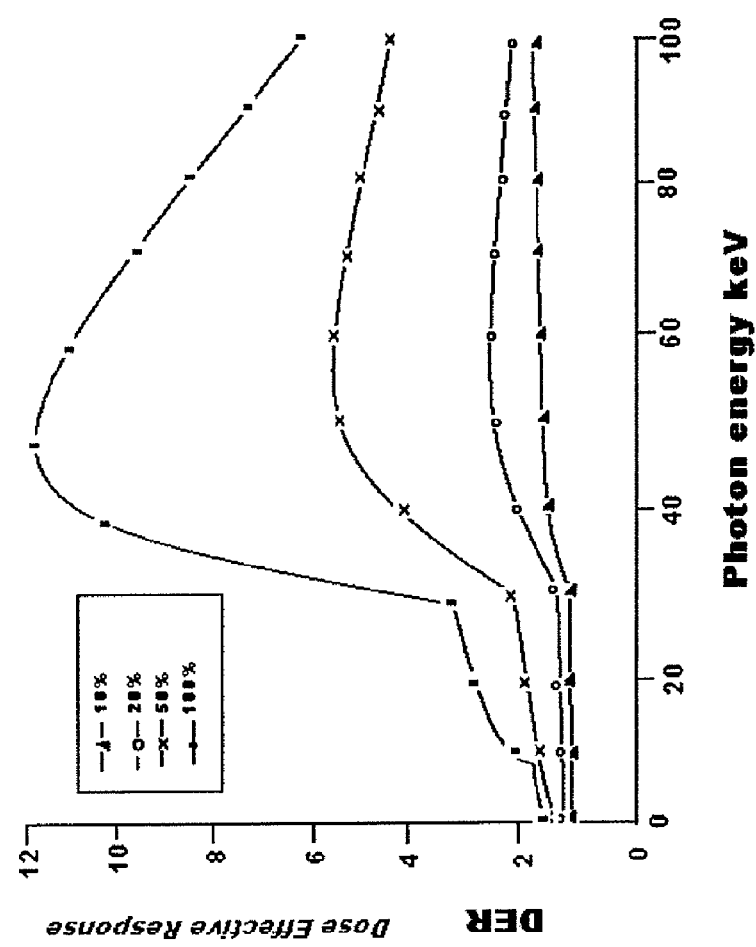
FIG. 8 shows a graph of the relationship between dose effective response, photon energy, and amount of a target atom in the DNA of a target tissue.

FIG. 8 shows a graph of the relationship between dose effective response, photon energy, and amount of a target atom in the DNA of a target tissue. Specifically, FIG. 8 shows the progressive improvement in the dose effective response with increasing photon energy delivered to a tumor containing progressively greater amounts of iodine containing deoxyuridine that has been substituted for thymidine in DNA strands. Dose effective response (DER) is a measure of effectiveness of a radiotherapy treatment. The graph in FIG. 8 shows that a higher concentration of target atoms results in a more effective treatment. Additionally, FIG. 8 shows that an optimal photon energy exists (as peaks in the curves in FIG. 8 at approximately 50 keV) for a particular concentration of target atoms. Specifically, a concentration of 100% of target atoms, a concentration of 50% of target atoms, and a concentration of 20% of target atoms each have a maximum DER for a photon energy of approximately 50 keV. Similarly, a concentration of 10% of target atoms, for example, achieves a substantially maximum DER for a photon energy of approximately 50 keV. Thus, the type and concentration of target atom to be used can be selected during pre-treatment planning to determine an optimal energy at which to provide radiation at the target.

FIG. 9 shows a flowchart of a process for pre-treatment radiotherapy planning, according to an embodiment of the invention. As shown in FIG. 9, pre-treatment radiotherapy planning 900 includes diagnosis 910, disease characterization 920, determination of appropriate drug 930, and treatment plan determination 940. Diagnosis 910 can be any disease diagnosis or identification technique including, for example, biopsy, imaging, for example, imaging with the x-ray source, and/or blood testing. After diagnosis 910, properties or characteristics of the disease are determined in disease characterization 920. Disease characterization 920 can include, for example, determining the extent or coverage of the disease, determining the size or a tumor, determining the density or a tumor, and/or determining the location of a tumor within the body of the patient. In some embodiments, as shown in FIG. 9, diagnosis 910 and disease characterization 920 can be used to determine the appropriate drug 930, for example, to determine the type of drug or target atom to be administered to the patient. Disease characteristics such as tumor density, location, and/or size, for example, can be used to select a drug or target atom that will result in effective or even optimal treatment. The drug or target atoms can be administered to the target tissue or tumor using known techniques including, for example, oral, intravenous, surgical, and/or gene therapy techniques. In some embodiments, no drug or target atoms are administered to the patient. For example, treatment of some diseases can be effected by radiating a target tissue or tumor with radiation at a specific energy at the target tissue along multiple paths without the use of drugs, for example, by using target atoms that have accumulated within an organ or tissue as a secondary consequence of the disease itself. After diagnosis 910, disease characterization 920, and determination of appropriate drug 930, a treatment plan is output in determine treatment plan 940. Determine treatment plan 940 can include, for example, estimating a dose effective response (DER), calculating doses of radiation to be emitted using various models such as, for example, a Geant code, a reverse Monte Carlo model, and/or a Monte Carlo N-Particle code (MCNP). In some embodiments, determine treatment plan 940 can include imaging after administration of a drug or target atom to evaluate changes in the target tissue or tumor and altering the treatment plan based on changes in the target tissue or tumor.

In some embodiments, a treatment plan output in determining a treatment plan 940 can include, for example, the types and/or amount of tissue or material that will be traversed by a radiation beam before the radiation beam reaches the target tissue or tumor from each direction or angle, the desired energy of the radiation beam at the target, the size of the target tissue or tumor, the quantity of target atoms within the tumor, and/or positions from which tunable a radiation source will radiate the target tissue or tumor. In other embodiments, a treatment plan can include information about the DER and concentration of target atoms in the target tissue or tumor. In yet other embodiments, a treatment plan can include instructions for observing a target tissue or tumor after treatment to determine whether the treatment was effective and/or whether further treatment is necessary or desirable. Additionally, in some embodiments, a treatment plan can be provided to a processor for implementing a treatment plan as described above.

In one embodiment, tunable radiation source 210 is fixedly positioned and a patient having a tumor is positioned on a positioning device such as, for example, a movable table. A treatment plan is provided to processor 230 including, for example, a first angle value, an energy value associated with the first angle, a second angle value, and an energy value associated with the second angle. The first angle can be associated with a first path of output radiation from tunable radiation source 210 relative to the tumor or other target tissue, and the second angle can be associated with a second path of output radiation from tunable radiation source 210 relative to the tumor or other target tissue Alternatively, a treatment plan can include, for example, a first angle value or a first position value, an energy value associated with the first angle value or the position value, a displacement value, and a second energy value. The displacement value can indicate or represent a rotation or movement in a two- or three-dimensional space, for example. In some embodiments, the treatment plan can include, for example, a first angle value and a second angle value, and processor 230 can access a lookup table to determine energy values based on angle values provided in the treatment plan. In yet other embodiments, the treatment plan includes more than two energy values, associated with angle values, and/or displacement values for radiating a tumor to treat a disease. Processor 230 can use the treatment plan to, for example, provide radiation at the first energy to the tumor from the first angle and provide radiation at the second energy to the tumor from the second angle.

Processor 230 can be operatively coupled to a system controller (not shown) configured to control tunable radiation source 210. Processor 230 can provide to the system controller signals associated with the first energy of a radiation beam to be output from tunable radiation source 210. In some embodiments, processor 230 can provide to the system controller signals associated with a desired energy of a radiation beam at a tumor and additional data such as tumor depth, an angle, and/or concentration of target atoms, for example. The system controller can determine, based on the desired energy at the tumor and the additional data, an energy of a radiation beam to be output from tunable radiation source 210 to provide a radiation beam at the desired energy at the tumor.

In some embodiments, the system controller can provide to tunable radiation source 210 signals associated with an energy of an output radiation beam. Tunable radiation source 210 can include a vector modulator operatively coupled to the system controller and a machine for producing pulsed, tunable, monochromatic x-rays (PTMX machine). In one embodiment, the vector modulator can receive signals from the system controller to modulate, for example, the phase and/or amplitude of an RF source to tune (e.g., adjust, modify or select) an output radiation beam of tunable radiation source 210. For example, tunable radiation source 210 can include an RF driver, such as an RF LINAC, that can be modulated in frequency and/or amplitude to tune the energy (wavelength or frequency) of an output of tunable radiation source 210. An output of the modulated RF source can be provided to a PTMX machine to generate a radiation beam such as, for example, a pulsed x-ray beam.

In some embodiments, detector 220 can be used to image the tumor in the body of the patient based on the radiation beam from tunable radiation source 210. In other embodiments, radiotherapy system 200 includes a radiation source (not shown) separate from tunable radiation source 210 for imaging with detector 220. Detector 220 can provide signals to a machine vision processor (not shown) configured to identify changes in position of the tumor with respect to the output radiation beam from tunable radiation source 210 based on, for example, machine vision techniques. For example, detector 220 can be an image detector that images the tumor at a first time and a second time from a fixed position. Machine vision processor can receive signals associated with the images produced by detector 220 at the first time and the second time, and determine the position of the tumor in each image and a positional variation of the tumor in each image. Machine vision processor can then determine the amount of positional variation of the tumor in, for example, the x-plane, y-plane, and/or z-plane. In some embodiments, the machine vision processor can be implemented in processor 230. In other embodiments, the machine vision processor can be implemented as a discrete component (not shown in FIG. 2) of radiotherapy system 200, for example, in a processor other than processor 230.

The machine vision processor can determine whether the tumor has changed position relative to the output radiation beam from tunable radiation source 210 and provide signals to correct for changes or shifts in the position of the tumor relative to the output radiation beam from tunable radiation source 210; these signals can be used, for example, to alter the path of the output radiation beam relative to the tumor or target tissue. In some embodiments, the machine vision processor can provide such signals to processor 230, and processor 230 can provide signals to tunable radiation source 210, to cause a change in the path of the output radiation beam relative to the tumor by changing the position of tunable radiation source 210 as described above. In other embodiments, processor 230 can be operatively coupled and provide signals to a table controller (not shown) coupled to the movable table. The table controller can, for example, receive signals from processor 230 and cause a change in position of the movable table in relation to tunable radiation source 210. In yet other embodiments, the machine vision processor can provide signals to tunable radiation source 210 and/or a table controller to correct for changes or shifts in the position of the tumor relative to the output radiation beam from tunable radiation source 210. In yet other embodiments, one or more optical elements (not shown) such as, for example, mirrors can be positioned between tunable radiation source 210 and the target tissue. These optical elements can move and/or be moved to change the path of the output radiation beam relative to the tumor. A mirror can, for example, include a motor, solenoid, and/or other positioning device operatively coupled to processor 230 configured to receive signals from processor 230 to cause a change in the position and/or orientation of the mirror relative to tunable radiation source 210 and/or the target tissue. In other embodiments, the optical element can be a tunable optical element such as an acousto-optical device that is operatively coupled to processor 230 and configured to receive signals from processor 230 to tune the optical element to change the path of the output radiation beam relative to the target tissue. In some embodiments, the optical element can be included in tunable radiation source 210.

In some embodiments, the correction for changes or shifts in the position of the tumor relative to the output radiation beam from tunable radiation source 210 can include tuning the output radiation beam from tunable radiation source 210. Similar to correcting for the change in position as described above, such tuning can be effected by, for example, processor 230 or the machine vision processor. In other embodiments, the table controller can be operatively coupled to tunable radiation source 210 and can access a lookup table to determine an appropriate energy of the output radiation beam from tunable radiation beam to effect the tuning based on a change in position of the table. In yet other embodiments, tunable radiation source 210 can access a lookup table to determine an appropriate energy of the output radiation beam from tunable radiation beam to effect the tuning based on a change in position of tunable radiation source 210.

In some embodiments, the corrections described above can be stored in a lookup table, for example, a correctional matrix relating angle of correction to an appropriate energy of output radiation beam from tunable radiation source 210. The correctional matrix can be further related to movements of patients such as, for example, movement due to respiratory or cardiac cycles. Processor 230, a table controller, and/or tunable radiation source 210 can use the correctional matrix to anticipate appropriate correction for patient movement.

In one embodiment, a method includes applying an output of a substantially monochromatic x-ray beam source to a target tissue along a first path, tuning the output of the substantially monochromatic x-ray beam source, and applying an output of a substantially monochromatic x-ray beam source to a target tissue along a second path different from the first path. The energy of the output of the substantially monochromatic x-ray beam source at the target tissue substantially corresponds to a binding energy level of an electron shell in an atom within the target tissue along the first path. The tuning tunes the substantially monochromatic x-ray beam source such that an energy of the output of the substantially monochromatic x-ray beam source at the target tissue along the second path substantially corresponds to a binding energy level of an electron shell in an atom within the target tissue.

In another embodiment, a method comprises applying an output of a substantially monochromatic x-ray beam source to a target tissue in a patient, identifying a location of the target tissue at a first time, tuning the substantially monochromatic x-ray beam source, and applying the output of a substantially monochromatic x-ray beam source to the target tissue at a second time no earlier than the first time. An energy of the output from the substantially monochromatic x-ray beam source at the target tissue substantially corresponds to a binding energy level of an electron shell in an atom within the target tissue. The tuning tunes the substantially monochromatic x-ray beam source such that an energy of the substantially monochromatic x-ray beam source at the target tissue substantially corresponds to a binding energy level of an electron shell in an atom within the target tissue at the first time based on the location of the target tissue at the first time.

In yet another embodiment, an apparatus comprises a tunable substantially monochromatic x-ray beam source, a positioning device, an image detector, and a processor. The positioning device is configured to change position of the output of the tunable substantially monochromatic x-ray beam source relative to a patient. The image detector is configured to image a target tissue within a body of a patient to produce data associated with images of the target tissue within the body of the patient. The processor is communicatively coupled to the image detector and the tunable substantially monochromatic x-ray beam source. The processor is configured to receive the data associated with images of the target tissue from the image detector, and effect an adjustment to the tunable substantially monochromatic x-ray beam source such that an energy of the output of the substantially monochromatic x-ray beam source at the target tissue substantially corresponds to a binding energy level of an electron shell in an atom within the target tissue based on the data associated with images of the target tissue.

In other embodiments, the methods and systems described above can be used for imaging the body of a patient. In such embodiments, the tunable radiation source can be tuned such that a radiation beam output from the tunable radiation source has an energy at a target tissue that is appropriate for imaging rather than for treating the target tissue. Thus, radiation beams having a highly specific energy at a target tissue can radiate or illuminate the target tissue along a number of paths and/or from a variety or angles or directions. In some embodiments, the imaging and treatment can be effected at the same time or during overlapping time periods based on multiple tunable radiation sources or target atoms in the target tissue having binding energies similar to energies appropriate for imaging the target tissue, for example. In yet other embodiments, a system can include two radiations sources. One radiation source can be a tunable radiation source for treating, for example, a target tissue or tumor within the body of a patient. The other radiation source can be used for imaging the target tissue or tumor, for example.

While certain embodiments have been shown and described above, it will be understood by those skilled in the art that various changes in form and details may be made. For example, some embodiments that have been described in relation to the treatment of tumors within the body of a patient can be useful in the treatment of other diseases or diseased tissues. Other embodiments that have been described in relation to the treatment of tumors can be useful for imaging a tumor or target tissue. Yet other embodiments that have been described with reference to x-rays can be used with other radiation beams including, for example, lasers. Similarly, some embodiments have been described as producing a radiation beam at an energy at a target that is substantially the same when emitted from multiple directions, angles or positions. It should be understood that, in some embodiments, it may be advantageous or desirable to produce a radiation beam that has a specific energy at the target for each direction or position and that the methods and systems described herein can be used in such embodiments. For example, a treatment plan can specify the peak energy of a radiation beam for each direction or position to produce a radiation beam at the desired energy at the target for each direction or position. Furthermore, it should be understood that the systems and methods described herein can include various combinations and/or sub-combinations of the components and/or features of the different embodiments described.

What is claimed is:

1. A method, comprising:
    applying an output of a substantially monochromatic x-ray beam source to a target tissue along a first path, an energy of the output of the substantially monochromatic x-ray beam source at the target tissue substantially corresponding to a binding energy level of an electron shell in an atom within the target tissue;
    tuning the substantially monochromatic x-ray beam source such that an energy of the output of the substantially monochromatic x-ray beam source at the target tissue along a second path substantially corresponds to a binding energy level of an electron shell in an atom within the target tissue; and
    applying the output of the substantially monochromatic x-ray beam source to the target tissue along the second path, the second path being different from the first path.

2. The method of claim 1, further comprising:
    changing a position of the output of the substantially monochromatic x-ray beam source relative to the target tissue from the position associated with the first path to a position associated with the second path.

3. The method of claim 1, wherein the tuning includes changing a frequency of the output of the substantially monochromatic x-ray beam source during operation of the substantially monochromatic x-ray beam source.

4. The method of claim 1, wherein the tuning includes changing a frequency of the output of the substantially monochromatic x-ray beam source after an output pulse of the substantially monochromatic x-ray beam source along the first path and before an output pulse of the substantially monochromatic x-ray beam source along the second path.

5. The method of claim 1, wherein the tuning is based on an energy from a plurality of predetermined energies identified during a pre-treatment analysis of the target tissue.

6. The method of claim 1, wherein the tuning is based on a distance between the substantially monochromatic x-ray beam source and the target tissue within a body of a patient.

7. The method of claim 1, further comprising:
    determining a plurality of paths of the output of the substantially monochromatic x-ray beam source relative to the target tissue and a plurality of frequencies of the output of the substantially monochromatic x-ray beam source,
    each path from the plurality of paths being associated with a frequency from the plurality of frequencies such that, for each path from the plurality of paths, the output of the substantially monochromatic x-ray beam source at the associated frequency from the plurality of frequencies has an energy at the target tissue substantially corresponding to a binding energy level of an electron shell in an atom within the target tissue.

8. A method, comprising:
    applying at a first time an output of a substantially monochromatic x-ray beam source to a target tissue in a body of a patient, an energy of the output at the first time from the substantially monochromatic x-ray beam source at the target tissue substantially corresponding to a binding energy level of an electron shell in an atom within the target tissue;
    identifying a location of the target tissue after the applying at the first time;
    tuning the substantially monochromatic x-ray beam source such that an energy of an output at a second time of the substantially monochromatic x-ray beam source at the target tissue substantially corresponds to the binding energy level of the electron shell in the atom within the target tissue based on the location of the target tissue, the second time being no earlier than the first time;
    applying the output of the substantially monochromatic x-ray beam source to the target tissue at the second time;
    identifying a location of the target tissue at a third time no earlier than the second time;
    determining a positional variation of the location of the target tissue at the third time relative to the location of the target tissue at the second time; and
    changing a path of the output of the substantially monochromatic x-ray beam source relative to the target tissue such that an energy of the output of the substantially monochromatic x-ray beam source at the target tissue at a fourth time substantially corresponds to the binding energy level of the electron shell in the atom within the target tissue at the fourth time, the fourth time being no earlier than the third time.

9. The method of 8, further comprising:
    determining the energy at the second time substantially corresponding to the binding energy level of the electron shell in the atom within the target tissue based on the location of the target tissue at the second time.

10. The method of claim 8, wherein the tuning includes changing a frequency of the output of the substantially monochromatic x-ray beam source.

11. The method of claim 8, further comprising:
    determining a plurality of paths of the output of the substantially monochromatic x-ray beam source relative to the target tissue and a plurality of frequencies of the output of the substantially monochromatic x-ray beam source, each path from the plurality of paths being associated with a frequency from the plurality of frequencies such that, for each path from the plurality of paths, the output of the substantially monochromatic x-ray beam source at the associated frequency from the plurality of frequencies has an energy at the target tissue substantially corresponding to a binding energy level of an electron shell in an atom within the target tissue.

12. The method of claim 8, wherein the tuning includes changing a frequency of the output of the substantially monochromatic x-ray beam source during operation of the substantially monochromatic x-ray beam source.

13. The method of claim 8, further comprising:
determining a pattern of repeating changes in position of the target tissue relative to the output of the substantially monochromatic x-ray beam source;
tuning an output of the substantially monochromatic x-ray beam source such that an energy of the output of the substantially monochromatic x-ray beam source at the target tissue substantially corresponds to the binding energy level of the electron shell in the atom within the target tissue based on the pattern of repeating changes in position of the target tissue relative to the output of the substantially monochromatic x-ray beam source.

14. An apparatus, comprising:
a substantially monochromatic x-ray beam source;
a positioning device, the positioning device being configured to define a plurality of paths of an output of the substantially monochromatic x-ray beam source relative to a patient;
an image detector, the image detector being configured to produce data associated with a target tissue within a body of the patient; and
a processor, the processor being communicatively coupled to the image detector and the substantially monochromatic x-ray beam source, the processor being configured to receive the data associated with the target tissue from the image detector, the processor being configured to effect an adjustment to the substantially monochromatic x-ray beam source such that an energy of the output of the substantially monochromatic x-ray beam source at the target tissue substantially corresponds to a binding energy level of an electron shell in an atom within the target tissue along the plurality of paths.

15. The apparatus of claim 14, wherein the substantially monochromatic x-ray beam source is configured to produce a pulsed output.

16. The apparatus of claim 14, wherein the substantially monochromatic x-ray beam source is configured to modify a frequency associated with the substantially monochromatic x-ray beam source after a first output pulse of the substantially monochromatic x-ray beam source and before a second output pulse of the substantially monochromatic x-ray beam source.

17. The apparatus of claim 14, wherein the processor is communicatively coupled to the positioning device, the processor configured to send signals to the positioning device to change a path from the plurality of paths for the output of the substantially monochromatic x-ray beam source relative to the patient.

18. The apparatus of claim 14, wherein the processor is configured to receive signals associated with a plurality of energies, the processor is further configured to tune the substantially monochromatic x-ray beam source based on the plurality of energies.

19. The apparatus of claim 14, wherein the processor is configured to determine the energy along a path from the plurality of paths substantially corresponding to the binding energy level of the electron shell in the atom within the target tissue for that path based on the data associated with the target tissue received.

* * * * *